(12) United States Patent
Vogel et al.

(10) Patent No.: US 7,054,684 B1
(45) Date of Patent: May 30, 2006

(54) PROTOCOL FOR BODY FAT MANAGEMENT

(75) Inventors: Richard C. Vogel, San Antonio, TX (US); David M. Tumey, San Antonio, TX (US)

(73) Assignee: TVX Internet Services, Inc., San Antonio, TX (US)

( * ) Notice: Subject to any disclaimer, the term of this patent is extended or adjusted under 35 U.S.C. 154(b) by 298 days.

(21) Appl. No.: 10/095,600

(22) Filed: Mar. 11, 2002

Related U.S. Application Data

(63) Continuation-in-part of application No. 09/933,030, filed on Aug. 20, 2001.

(51) Int. Cl.
*A61N 1/00* (2006.01)

(52) U.S. Cl. .......................................... 607/3
(58) Field of Classification Search ............. 607/1–156
See application file for complete search history.

(56) References Cited

U.S. PATENT DOCUMENTS

| | | | | |
|---|---|---|---|---|
| 5,913,836 A | * | 6/1999 | Groux | 601/21 |
| 2002/0055762 A1 | * | 5/2002 | Gliner | 607/46 |
| 2002/0058906 A1 | * | 5/2002 | Lebel et al. | 604/65 |

* cited by examiner

*Primary Examiner*—Scott M. Getzow
(74) *Attorney, Agent, or Firm*—Wayne J. Colton, Inc.

(57) ABSTRACT

A protocol for body fat management comprises the steps of stimulating the release of free fatty acids into the bloodstream of a person and, within 20 minutes thereafter, ingesting into the person a collagen-based formula. The stimulating step may be conducted by delivering a low voltage alternating current to the person's body, which may be accomplished utilizing an electronic stimulation device to deliver the current to the feet of the person. The device may be provided with the capability for adjustment of both the voltage level and frequency of the current as well as the capability to enable operation of the device only upon payment to a service provider of a fee.

11 Claims, 7 Drawing Sheets

PROTOCOL FOR BODY FAT MANAGEMENT

RELATED APPLICATION

The present application is a continuation-in-part, under 35 U.S.C. § 120, of Applicant's co-pending U.S. patent application Ser. No. 09/933,030 filed Aug. 20, 2001. By this reference, the entire disclosure of U.S. patent application Ser. No. 09/933,030 is incorporated herein as though now set forth in its entirety.

FIELD OF THE INVENTION

The present invention relates to systems and methods for weight loss and body fat management. More particularly, the invention relates to methods and apparatus wherein previously proposed weight loss modalities are combined in a manner designed to produce weight loss results not available through their individualized or uncoordinated usage.

BACKGROUND OF THE INVENTION

Collagen-based formulas have been reported to increase lean body muscular mass and promote fat loss when taken as a dietary supplement. Although the exact physiology is not known, it is believed that the collagen-based formula enhances the known physiological processes for the metabolism of fat and muscle as influenced by the complex interplay between insulin, exercise and stress and other hormones. Regardless of the physiological basis, however, the reported weight loss results speak for themselves.

Other unrelated studies have reported that persons receiving mild electrical currents into their bodies have experienced weight loss. While the underlying causes for the weight loss are not completely understood, it is believed that the electrical currents cause the sympathetic nervous system to produce catecholemines, which in turn attach to receptor sites on fat cells. As a result, it is believed that free fatty acids are released into the blood stream. Depending on the user's exercise regime and dietary habits, the released free fatty acids may be converted to more useful products.

Although each of the foregoing modalities is associated with weight loss, no suggestion for their combination has been made. Applicant has found, however, that the combination of the foregoing modalities according to a strictly timed protocol can produce weight loss results far faster either modality alone or through the combination of the foregoing modalities in noncompliance with the discovered time protocol. It is therefore an overriding object of the present invention to set forth a protocol for combining electrical stimulation therapy with the ingestion of a collagen-based formula such that results in synergistic weight loss.

SUMMARY OF THE INVENTION

In accordance with the foregoing objects, the present invention—a protocol for body fat management—generally comprises the steps of stimulating the release of free fatty acids into the bloodstream of a person and, within 20 minutes thereafter, ingesting into the person a collagen-based formula. The stimulating step may be conducted by delivering a low voltage alternating current to the person's body, which may be accomplished utilizing an electronic stimulation device to deliver the current to the feet of the person. The device may be provided with the capability for adjustment of both the voltage level and frequency of the current as well as the capability to enable operation of the device only upon payment to a service provider of a fee.

Finally, many other features, objects and advantages of the present invention will be apparent to those of ordinary skill in the relevant arts, especially in light of the foregoing discussions and the following drawings, exemplary detailed description and appended claims.

BRIEF DESCRIPTION OF THE DRAWINGS

Although the scope of the present invention is much broader than any particular embodiment, a detailed description of the preferred embodiment follows together with illustrative figures, wherein like reference numerals refer to like components, and wherein.

DETAILED DESCRIPTION OF THE PREFERRED EMBODIMENT

Although those of ordinary skill in the art will readily recognize many alternative embodiments, especially in light of the illustrations provided herein, this detailed description is exemplary of the preferred embodiment of the present invention, the scope of which is limited only by the claims appended hereto.

Figure 1:
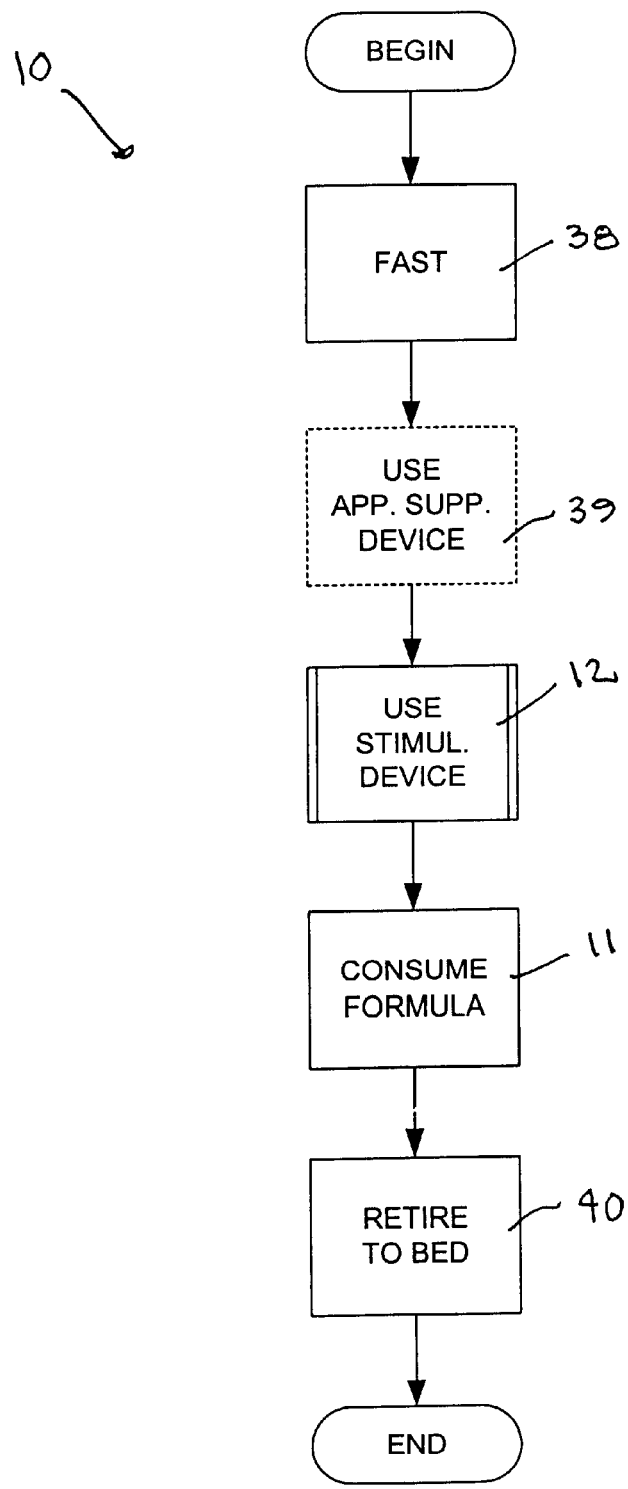
FIG. 1 shows, in a flowchart, the preferred body fat management protocol of the present invention.

Referring now to the figures, and to FIG. 1 in particular, the preferred weight loss protocol 10 of the present invention is shown to generally comprise the ingestion 11 of a collagen-based formula within a critical time window following the usage 12 of an electronic stimulation device 13. As will be better understood further herein, the electronic stimulation device 13 serves to stimulate reduction of fat cells as a key part of the novel weight loss protocol 10. In particular, Applicant has found that ingestion 11 of a collagen-based formula on an empty stomach and within 20 minutes following usage 12 of the electronic stimulation device 13 produces weight loss results not attainable through the independent, uncoordinated usage 12 of the electronic stimulation device 13 and ingestion 11 of the collagen-based formula.

Figure 2:
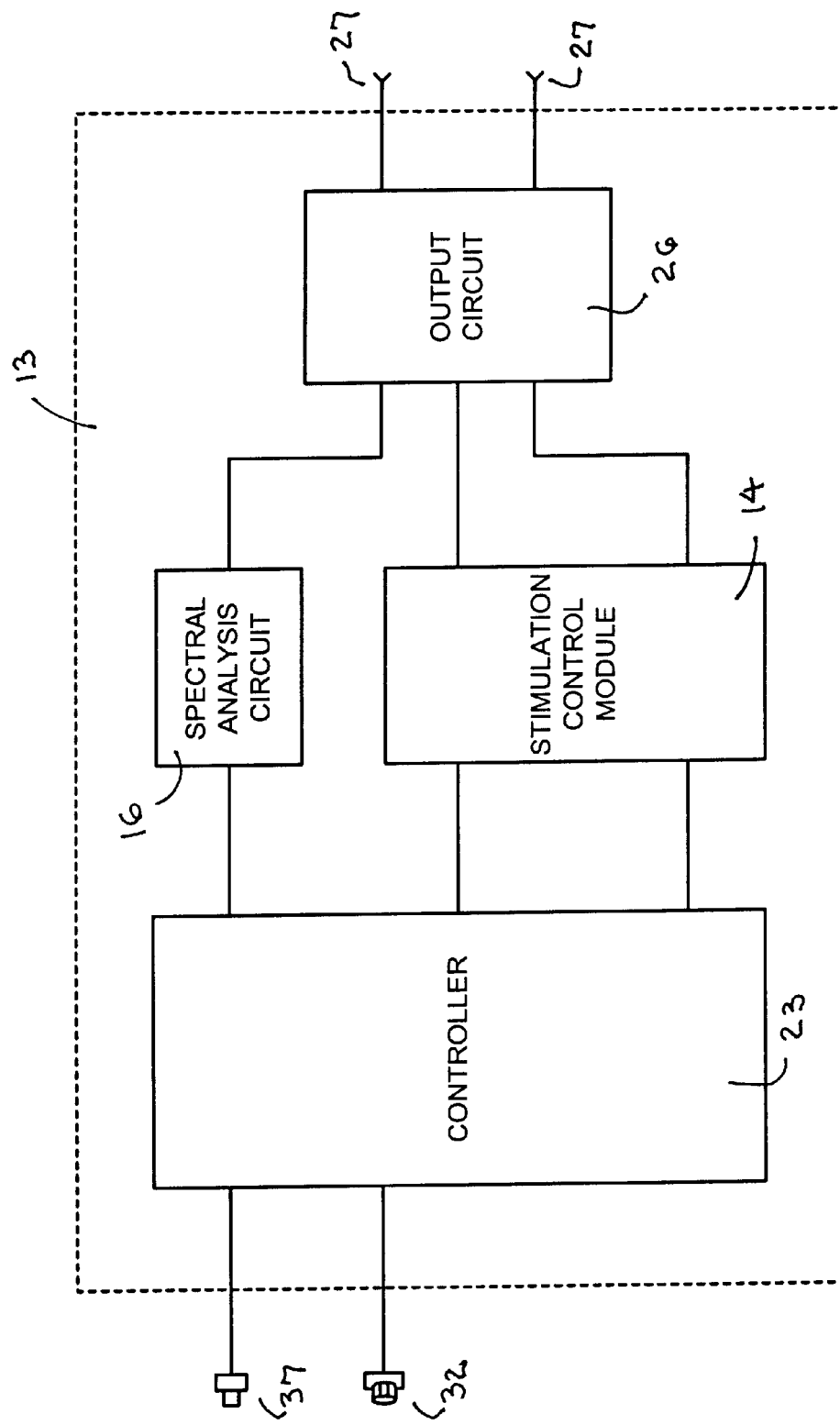
FIG. 2 shows, in a functional block diagram, details of an electronic stimulation device utilized as part of the protocol of FIG. 1.

As shown in FIG. 2, the preferred embodiment of the electronic stimulation device 13 generally comprises a stimulation control module 14, adapted to deliver 15 a low current voltage to the user's body, and a spectral analysis circuit 16, adapted to determine 17 the optimum frequency for conduction into the user's body of the low current voltage. Although much of the benefit of the present invention may be attained utilizing a simplified version of the electronic stimulation device 13 having the minimal capability to deliver 15 a low current voltage to the user's body, those of ordinary skill in the art will recognize, in light of this exemplary disclosure, that the features of the preferred embodiment directed toward adjustment of voltage level and treatment frequency are highly desirable in order to ensure that the user receives the maximum weight loss benefit available from the described protocol 10. In any case, the preferred embodiment of the invention utilizes a pair of specially manufactured, electrically conductive "socks" or "slippers," or the substantial equivalent thereof, to provide electrical contact between the electronic stimulation device 13 and the user's feet. Appropriate socks and slippers are described in detail in Applicant's co-pending U.S. patent application filed on Mar. 11, 2002 in the names of David M. TUMEY and Teryl B. SANDERS, which by this reference is incorporated herein as though now set forth in its entirety.

Figure 3:
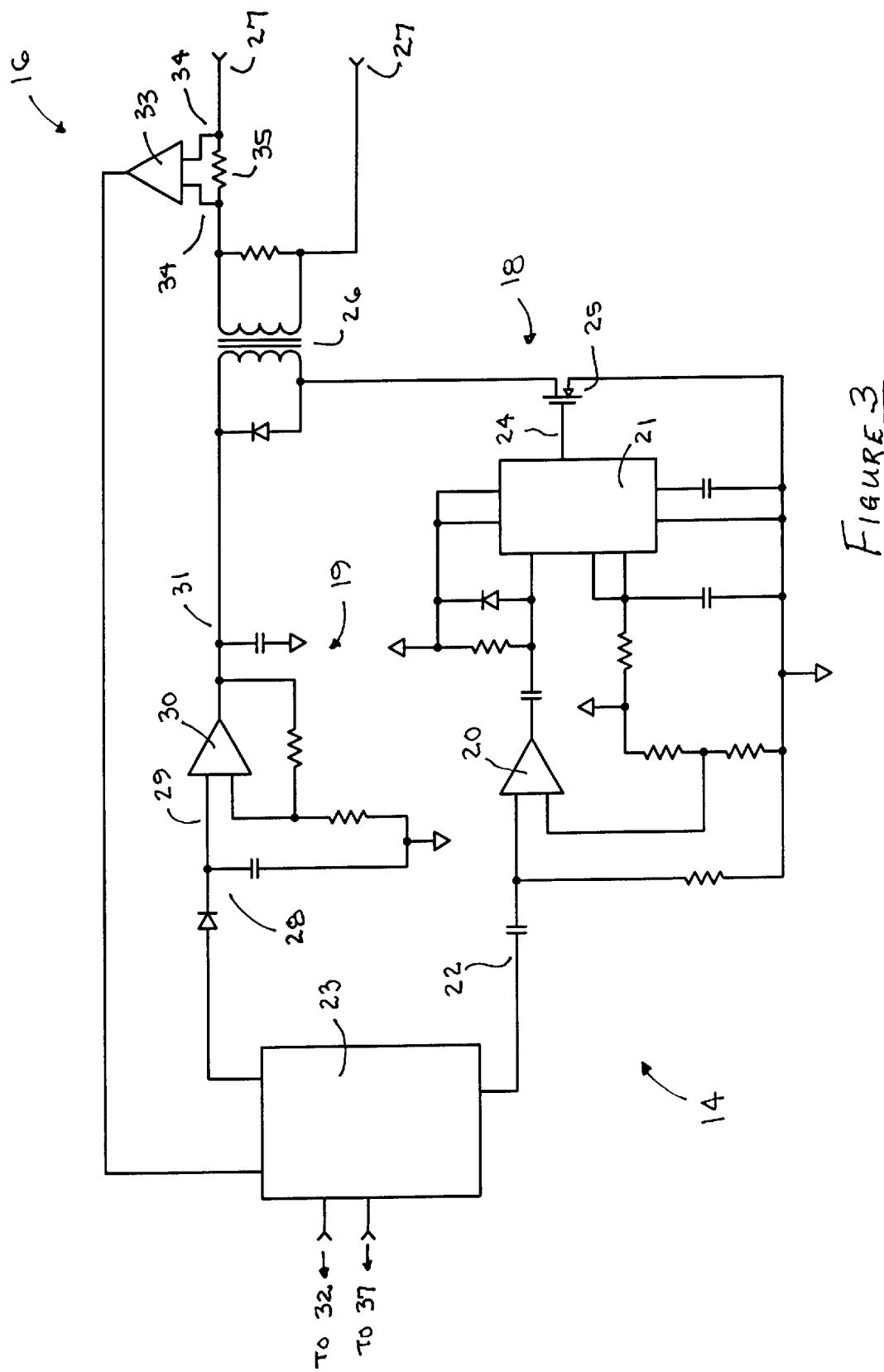
FIG. 3 shows, in a schematic diagram, details of the electronic stimulation device of FIG. 2.

As shown in FIG. 3, the preferred embodiment of the stimulation control module 14 comprises a frequency control circuit 18, for controlling the frequency of the delivered current signal, and a voltage control circuit 19, for controlling the amplitude of the delivered current signal. In particular, the frequency control circuit 18 comprises an operational amplifier 20, configured as a comparator, which in turn drives a 555 integrated circuit timer 21, configured as a monostable oscillator, according to the level of an input signal. As will be better understood further herein, the input 22 to the comparator 20 is interfaced to a controller 23, which provides the input signal according to a determination utilizing the spectral analysis circuit 16 of which frequency is best conducted into the feet of the user. The output 24 from the monostable oscillator is then utilized to drive the gate of a medium power MOSFET 25. The transistor's source and drain circuits are in series with a 10 to 1 step-up transformer 26, which interfaces the stimulation control module 14 through a plurality of jacks 27 to the electrically conductive socks or slippers.

Likewise, the controller 23 is connected to an envelope detector 28 configured to drive the positive input 29 of an operational amplifier 30, the output 31 of which is also connected to the step-up transformer 26. The signal supplied from the controller 23 to the envelope detector 29 is determined based upon an adjustment made by the user through an appropriate input device such as, for example, a variable resistor 32 or the like. In this manner, both the amplitude and the frequency of the signal generated through the step-up transformer 26 may be controlled.

Finally, as also shown in FIG. 2, the spectral analysis circuit 16 generally comprises a current amplifier 33 having inputs 34 connected across a shunt resistor 35 in the output of the step-up transformer 26. In this manner, the current amplifier 33 may monitor current flow through the socks or slippers and into the user's feet. The output from the current amplifier 33 is then communicated to the controller 23 as part of a spectral sweep 36 to determine which frequency or frequencies are best conducted into the user's feet. In operation, the controller is adapted to generate 36 a sweep of frequencies (through the frequency control circuit 18) in response to an input from the user such as, for example, depression of a momentary switch 37 connected to an input to the controller 23. During the spectral sweep 36, the controller 23 is utilized to determine which frequency or frequencies are best conducted into the feet of the user. As described above, the determined best frequency is stored and utilized for the delivery 15 to the user of the stimulation voltage.

Referring again to FIG. 1, the preferred protocol of the present invention is detailed. According to the preferred protocol, a user wishing to lose weight with the assistance of the present invention is directed to fast 38 for at least three hours prior to bedtime. If, however, the user should have difficulty abstaining from food or carbonated or sugary beverages for the full three hour period, the present invention also comprises the utilization 39 of an electronic appetite suppressor. The electronic appetite suppressor generally comprises a headphone type device adapted to produce a mild electrical current at known acupuncture points near the ears which induces in the user a sense of well being similar to that obtained through acupuncture techniques. Exemplary of such an electronic appetite suppression device is that which is described in Applicant's co-pending U.S. patent application entitled "APPETITE SUPPRESSION DEVICE," filed in the name of David M. TUMEY on Feb. 4, 2002, which by this reference is incorporated herein as though now set forth in its entirety. In any case, the user then makes use 12 of the electronic stimulation device 13 during the final 10 minutes to one hour prior to bedtime. Use 12 of the electronic stimulation device 13 (as described in greater detail further herein) is thought to activate the sympathetic nervous system in the production of catecholemines. The produced catecholemines then attach to receptor sites on the user's fat cells, thereby releasing free fatty acids into the blood stream. Upon completion of the electronic stimulation therapy, the user consumes 11 a collagen-based formula and retires 40 to bed. As the user sleeps, the collagen-based formula utilizes the released free fatty acids for tissue, muscle and bone repair. In this manner, body fat is effectively is redistributed and converted into more healthy tissues.

Figure 4:
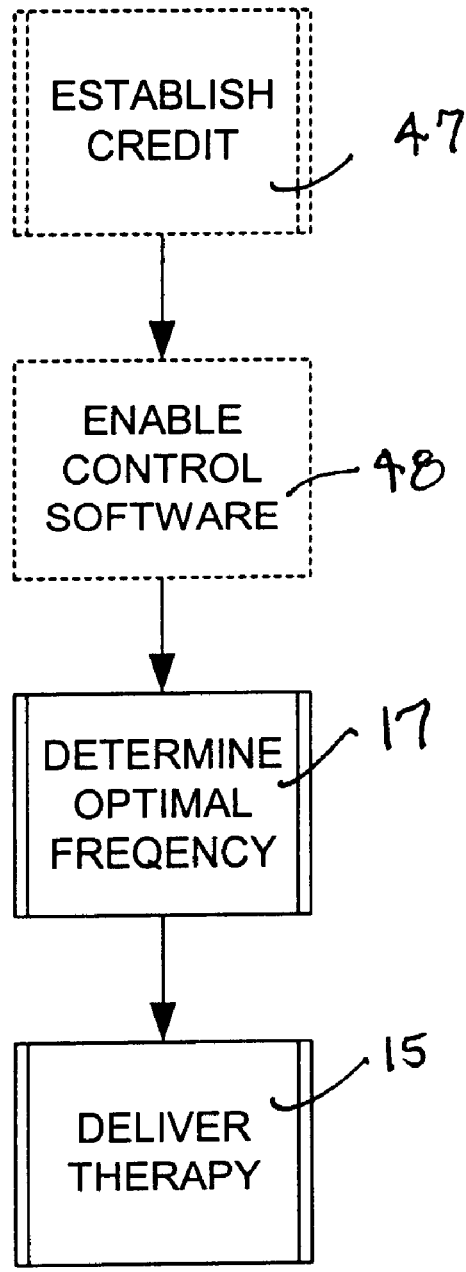
FIG. 4 shows, in flowchart, steps taken in the utilization of the electronic stimulation device of FIG. 2 within the protocol of FIG. 1.

As shown in FIG. 4, the use of the electronic stimulation device preferably begins with the user placing one foot only into each of either the socks or the slippers and sitting comfortably in a chair. The appropriate treatment frequency is then determined 17 and the therapy delivered 15, each as described in greater detail further herein. Although those of ordinary skill in the art will recognize that the treatment frequency may be manually selected or may be determined a priori based upon empirical data, it is preferred that an analysis be performed each time the electronic stimulation device 13 is utilized in order to determine 17 which frequency or frequencies are best conducted into the user's feet at that time. In this manner, factors such as hydration and the like may be accounted for, thereby ensuring that the user will receive the maximum benefit of the described protocol 10.

Figure 5:
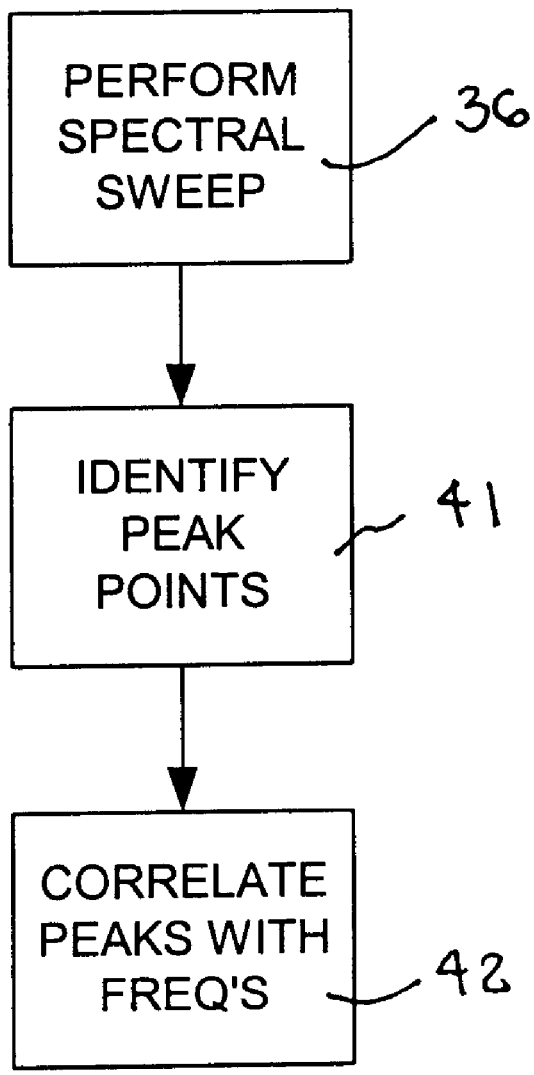
FIG. 5 shows, in flowchart, certain details of the utilization of the electronic stimulation device according to the steps outlined in FIG. 4.

As shown in FIG. 5, a low voltage and low current spectral sweep preferably encompassing frequencies from about 100 Hz to about 10 kHz is first performed 36 (at the direction of the user as determined by detecting depression of the switch 37 connected to the provided input to the controller 37). During the spectral sweep 36, the spectral analysis circuit 16 is utilized to measure the current conducted into the user's feet. The measurements are then processed to identify 41 the peak energy point or points, which are correlated 42 with the frequency or frequencies responsible for their generation.

Figure 6:
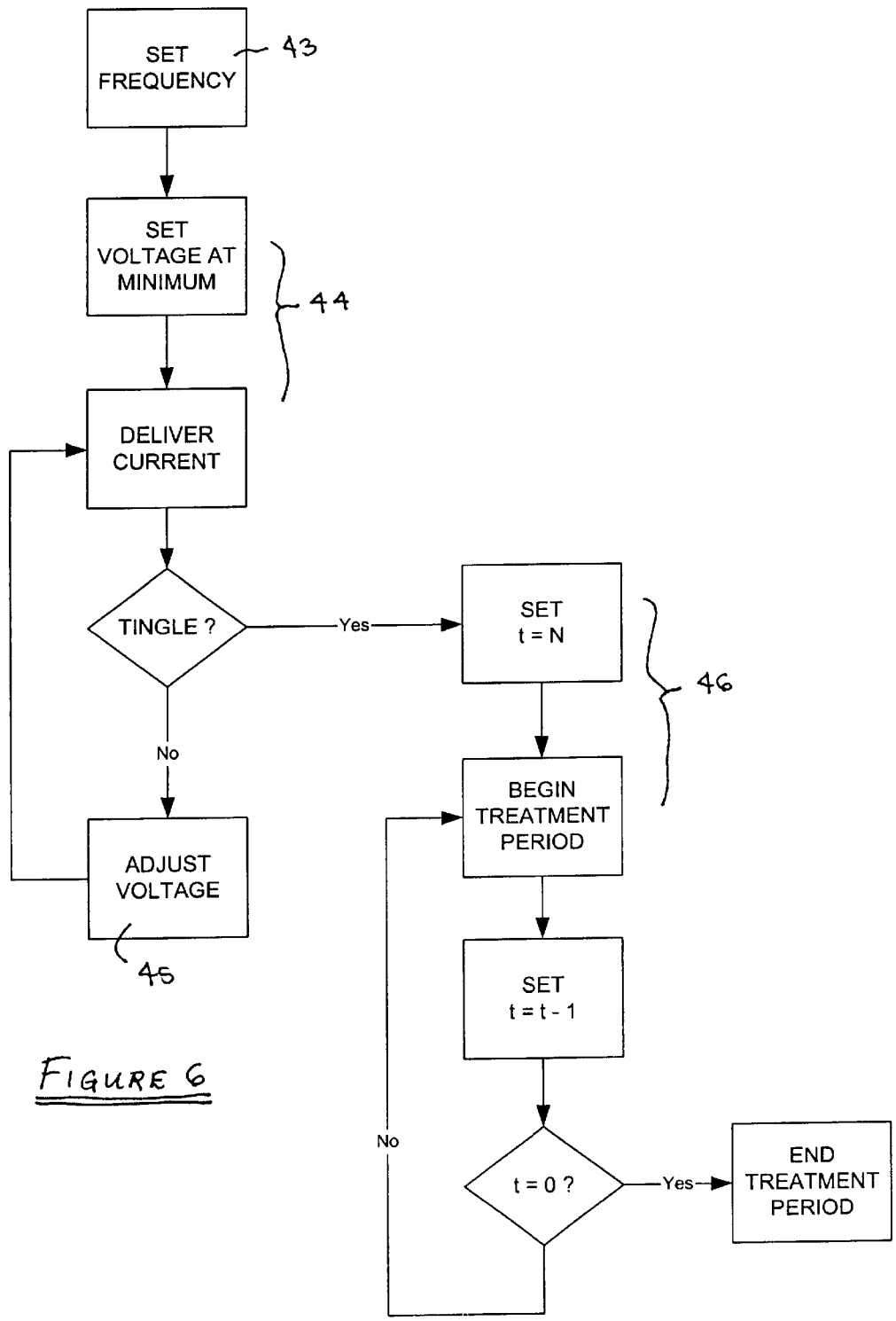
FIG. 6 shows, certain other details of the utilization of the electronic stimulation device according to the steps outlined in FIG. 4.

As detailed in FIG. 6, once the treatment frequency has been determined 42, the therapy is delivered 15 by first setting 43 the therapy frequency according to the previous determination 42. Under the control of the voltage control circuit 18, the lowest level current is then delivered 44 at the set treatment frequency through the socks or slippers to the user. The user then adjusts 45 the treatment voltage level, by adjustment of the input device 32 connected to the corresponding input to the controller 23, until a slight "tingling" sensation is felt in the feet. Upon generation of sufficient current to produce a tingling sensation indicative of current flow through the user's feet, a treatment timer is started 46 in order to deliver 15 8 to 20 minutes of therapy to the user, although up to one hour of therapy is thought to contribute to the synergistic weight loss results produced through the protocol 10 of the present invention.

Upon completion of the electronic stimulation, the user consumes 11 the collagen-based formula. As previously discussed, it is critical that this consumption take place within 20 minutes following the electronic stimulation 12 in order to achieve the synergistic effect of combining these weight loss modalities. Additionally, it is noted that the user should retire 40 to bed within about 15 minutes following consumption 11 of the collagen-based formula in order to ensure that the user's body is in a sleeping state for a substantial portion of the 90 minute window during which the collagen-based formula is most efficacious.

Figure 7:
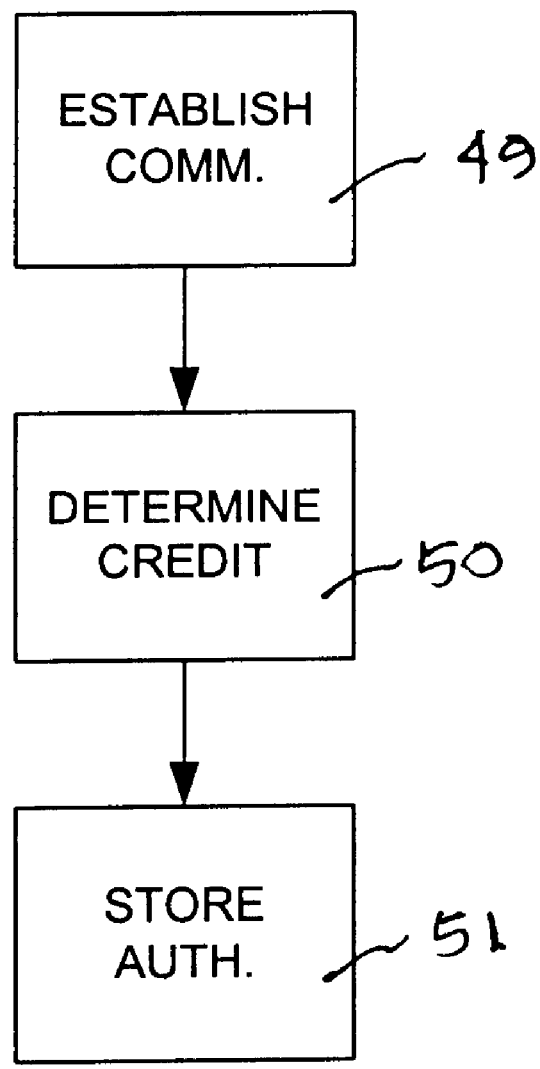
FIG. 7 shows, in flowchart, details regarding control of the electronic stimulation device of FIG. 2.

While the foregoing description is exemplary of the preferred embodiment of the present invention, those of ordinary skill in the relevant arts will recognize the many variations, alterations, modifications, substitutions and the like as are readily possible, especially in light of this description, the accompanying drawings and claims drawn thereto. For example, as shown in FIGS. 4 and 7, it may be desirable for the controlled commercialization of the described protocol 10 to provide a means by which the operation of the electronic stimulation device may be dependent upon satisfaction of some criteria, such as the establishment 47 of credit with a service provider. To this end, provision is made in at least one embodiment of the protocol 10 for the establishment 47 of credit as a prerequisite to the enabling 48 of the controller 23 for operation.

As shown in FIG. 7, the establishment 47 of credit may involve the periodic establishment 49 of communication with the service provider. As will be appreciated by those of ordinary skill in the art, the establishment 49 of communication may be through a MODEM connection, Internet connection or any substantial equivalent thereof. In any case, once it is determined 50 that the user is "paid up" or otherwise authorized to make use of the general protocol 10, appropriate authorization codes are stored 51 within the controller 23 in order that the user may then make use of the device at any time or place so long as his or her authorization remains valid. This may be for a number of therapy minutes or may be based upon the passage of a number of days or may be based upon any other substantially equivalent measurement technique. In any case, because the scope of the present invention is much broader than any particular embodiment, the foregoing detailed description should not be construed as a limitation of the scope of the present invention, which is limited only by the claims appended hereto.

What is claimed is:

1. A protocol for body fat management, said protocol comprising the steps of:

stimulating the release of free fatty acids into the bloodstream of a person;

ingesting into the person a collagen-based formula; and wherein said ingesting step is performed within 20 minutes following said stimulating step.

2. The protocol as recited in claim 1, wherein said stimulating step comprises delivering a low voltage alternating current to the person's body.

3. The protocol as recited in claim 2, wherein said delivering step comprises utilizing an electronic stimulation device to deliver said current to the feet of the person.

4. The protocol as recited in claim 3, wherein said electronic stimulation device comprises a voltage controller for adjusting the voltage level of said current.

5. The protocol as recited in claim 4, wherein said electronic stimulation device comprises a frequency controller for adjusting the frequency of said current.

6. The protocol as recited in claim 3, wherein said electronic stimulation device comprises a frequency controller for adjusting the frequency of said current.

7. The protocol as recited in claim 3, wherein said electronic stimulation device comprises a controller, said controller being programmed to operate only upon a predetermined condition.

8. The protocol as recited in claim 7, wherein said predetermined condition comprises payment by the person of a fee.

9. The protocol as recited in claim 1, said protocol further comprising the step of fasting by the person prior to said stimulating step.

10. The protocol as recited in claim 9, said protocol further comprising the step of sleeping by the person following said ingesting step.

11. The protocol as recited in claim 10, wherein said sleeping step begins within 15 minutes following said ingesting step.

* * * * *